United States Patent [19]

Shaw

[11] 4,209,017
[45] Jun. 24, 1980

[54] SURGICAL INSTRUMENT HAVING SELF-REGULATING RADIANT HEATING OF ITS CUTTING EDGE AND METHOD OF USING THE SAME

[76] Inventor: Robert F. Shaw, 50 St. Germain, San Francisco, Calif. 94114

[21] Appl. No.: 558,338

[22] Filed: Mar. 14, 1975

Related U.S. Application Data

[63] Continuation-in-part of Ser. No. 534,756, Dec. 2, 1974, Pat. No. 4,089,336, which is a continuation of Ser. No. 63,645, Aug. 13, 1970, abandoned, which is a continuation of Ser. No. 681,737, Nov. 9, 1967, abandoned.

[51] Int. Cl.$^2$ ............................................. A61B 17/36
[52] U.S. Cl. .................................. 128/303.1; 30/140; 219/227
[58] Field of Search ...................... 30/140, 346.53, 345; 128/303.1, 303.13, 303.14; 219/221, 223, 227, 228, 229, 230, 231

[56] References Cited

U.S. PATENT DOCUMENTS

| | | | |
|---|---|---|---|
| 1,456,639 | 5/1923 | Lagier | 30/140 X |
| 1,550,386 | 8/1925 | Neuwirth et al. | 219/228 X |
| 1,691,763 | 11/1928 | Kastner | 30/140 |
| 1,988,167 | 1/1935 | De Bats | 30/346.53 |
| 2,319,607 | 5/1943 | Kevorkian et al. | 30/345 |
| 2,338,007 | 12/1943 | Morris | 30/345 X |
| 3,514,856 | 6/1970 | Camp et al. | 30/346.53 |
| 3,659,332 | 5/1972 | Morrone | 30/140 X |
| 3,774,703 | 11/1973 | Sanderson | 30/346.53 X |

FOREIGN PATENT DOCUMENTS 448865  9/1927  Fed. Rep. of Germany ........... 219/233

Primary Examiner—Robert W. Michell
Assistant Examiner—Michael H. Thaler
Attorney, Agent, or Firm—Lyon & Lyon

[57] ABSTRACT

The cutting edge of a scalpel blade is heated to an elevated preselected constant operating temperature for cutting tissue with simultaneous hemostasis by radiant heating of the blade in the region along the cutting edge. Radiant energy is contained within the blade by a reflective coating over the transparent or translucent blade material. Heating along the cutting edge is provided by the disposition of a radiation-absorptive material beneath the reflective coating in the region along the cutting edge. Selective heating of regions of the cutting edge that are locally cooled by contact with tissues during surgical cutting is provided for by fabricating the radiation-absorptive element of the blade of a thermochromic material that exhibits a substantial increase in absorption coefficient for a temperature decrement within the operating temperature range.

19 Claims, 5 Drawing Figures

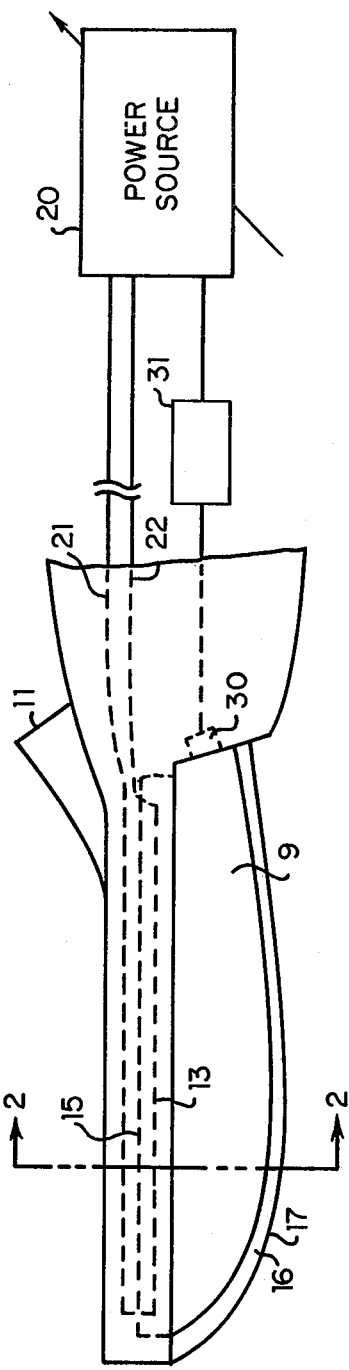
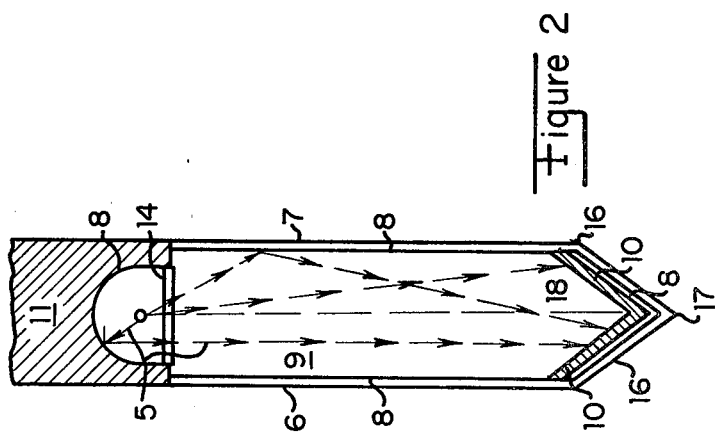
Figure 1
Figure 2

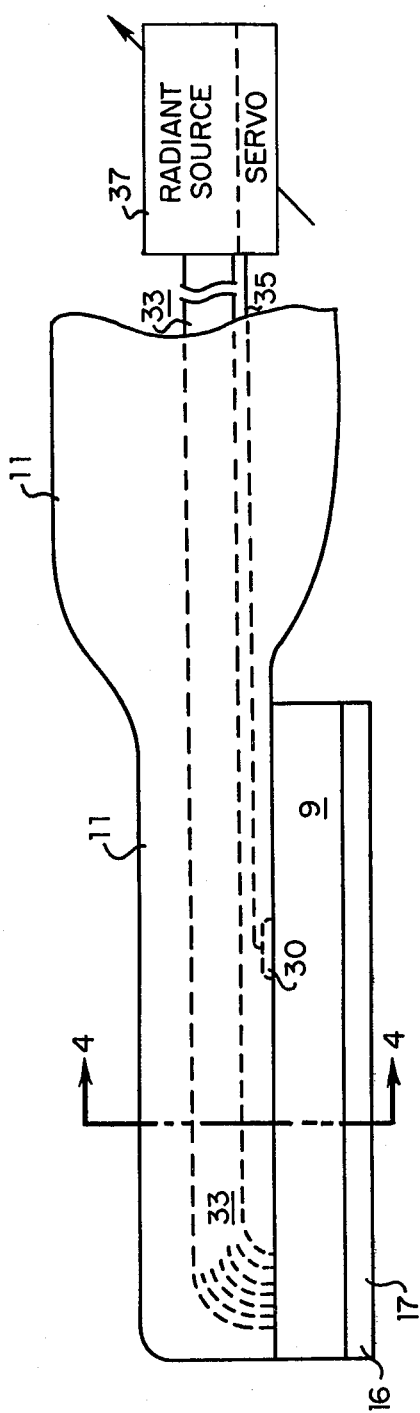
Figure 3
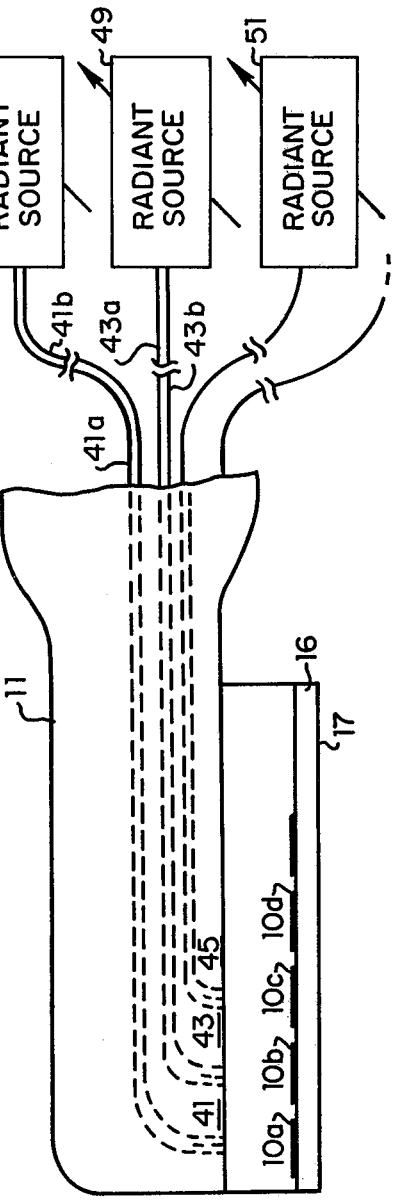
Figure 5
Figure 4

SURGICAL INSTRUMENT HAVING SELF-REGULATING RADIANT HEATING OF ITS CUTTING EDGE AND METHOD OF USING THE SAME

RELATED APPLICATIONS

This application is a continuation-in-part of U.S. Pat. Application Ser. No. 534,756 filed Dec. 2, 1974 now U.S. Pat. No. 4,089,336, which is a continuation of U.S. Patent Application Ser. No. 63,645, filed Aug. 13, 1970, now abandoned, which is a continuation of U.S. Patent Application Ser. No. 681,737 filed Nov. 9, 1967, now abandoned.

BACKGROUND OF THE INVENTION

The control of bleeding during surgery accounts for a major portion of the total time involved in an operation. The bleeding that occurs from the plethora of small blood vessels that pervade all tissues whenever tissues are incised obscures the surgeon's vision, reduces his precision, and often dictates slow and elaborate procedures in surgical operations. It is well known to heat the tissues to minimize bleeding from incisions, and surgical scalpels which are designed to elevate tissue temperatures and minimize bleeding are also well known. One such scalpel transmits high frequency, high energy sparks from a small electrode held in the surgeon's hand to the tissues, where they are converted to heat. Typically, substantial electrical currents pass through the patient's body to a large electrode beneath the patient, which completes the electrical circuit. Discharge of sparks and temperature conversion in the tissue are poorly controlled in distribution and intensity, and erratic muscular contractions in the patient are produced so that this apparatus cannot be used to perform precise surgery. Further, apparatus of this type frequently produce severe tissue damage and debris in the form of charred and dead tissue, which materially interfere with wound healing.

Another well-known surgical scalpel employs a blade with a resistive heating element which cuts the tissue and provides simultaneous hemostasis. Although these resistive elements can be readily brought to a suitably high and constant temperature in air prior to contacting tissues, as soon as portions of the blade come in contact with tissues, they are rapidly cooled. During surgery, non-predictable and continuously varying portions of the blade contact the tissues as they are being cut. As the blade cools, the tissue cutting and hemostasis become markedly less effective and tissue tends to adhere to the blade. If additional power is applied by conventional means to counteract this cooling, this additional power is selectively delivered to the uncooled portions of the blade, frequently resulting in excessive temperatures which may result in tissue damage and blade destruction. This results from the fact that in certain known resistively heated scalpels, the heating is a function of the current squared times the resistance ($I^2R$). In conventional metallic blades of this type, the higher the temperature of any blade portion, the greater its electrical resistance, and consequently the greater the incremental heating resulting from incremental power input.

It is generally recognized that to seal tissues and effect hemostasis it is desirable to operate at a temperature between 300° C. and 1000° C. And for reasons noted above, it is desirable that electrothermal hemostatic surgical cutting instruments include a mechanism by which power is selectively delivered to those portions of the cutting edge that are cooled by tissue contact so that the blade may be maintained at a substantially uniform operating temperature within the desired optimal range. Recently, hemostatic scalpels have been described (see, for example, U.S. Pat. Nos. 3,768,482 and 3,826,263) in which the temperature-controlling mechanisms include resistive heating elements disposed on the surface of the scalpel blade. However, such instruments require precision in fabricating the dimensions of the heating elements to obtain the desired resistances. And such resistive heating elements may be subjected to variations in resistance during use, as tissue juices and proteins become deposited upon the surface of the blade.

SUMMARY OF THE INVENTION

The present invention provides a surgical cutting instrument in which the cutting portion of the blade is brought to an elevated temperature by radiant heating of the internal structures of the blade. Radiant energy from a source such as a high temperature filament or gas discharge source is optically coupled to a substantially transparent blade-shaped structure, one edge of which has been sharpened to form the cutting edge of the instrument. A non-transmitting internally-reflecting surface prevents loss of radiant energy from within the blade. The resultant scattering of light by internal reflections tends to distribute radiant energy throughout the blade, and the optical scattering may be further enhanced by the incorporation of particulate scattering elements within the blade material.

Beneath the internally-reflecting coating and only along the cutting edge of the blade, there is disposed a radiation-absorbing material which absorbs and converts the radiant energy to heat which is conducted through the material to the cutting edge to bring it to operating temperatures. The average temperature along the cutting edge may be adjusted by adjusting the power supplied by the radiation source, for example, by adjusting the electrical signals applied thereto.

Selective heating of those portions of the cutting edge that are cooled by tissue contact in order to maintain cutting temperatures sufficiently constant (i.e., temperature self-regulation) may be accomplished by fabricating the radiation absorber in the region of the cutting edge of a material which substantially increases in absorption coefficient with decreasing temperature within the operating temperature range. Since each local region of the material absorbs the distributed radiation in accordance with its local absorption coefficient, each local region may have its temperature regulated independently of the operating temperature of adjacent regions. Thus, even in the presence of unpredictable and substantial variations in the cooling of the various regions of the heated edge resulting from the edge being manipulated to cut tissues, all regions along the length of the cutting edge can be maintained within a suitably constant temperature range. Known thermochromic materials which have absorption coefficients that vary as a function of temperature may be used as the radiation-absorbing material in the surgical instrument of the present invention.

DESCRIPTION OF THE DRAWINGS

FIG. 1 is a partial side view of a surgical cutting instrument according to one embodiment of the present invention;

FIG. 2 is an end view of the apparatus of FIG. 1 showing the blade-like element and the radiation source therein;

FIG. 3 is a partial side view of an alternative embodiment of the present invention;

FIG. 4 is an end view of the apparatus of FIG. 3 showing the optical channels therein for distributing radiation from a remote source; and FIG. 5 is a partial side view of another embodiment which employs segmented thermochromic regions.

DESCRIPTION OF THE PREFERRED EMBODIMENT

Referring now to FIG. 1, there is shown a partial side view of a surgical cutting instrument which has a blade-like element 9 that is suitably attached to handle 11. A high-intensity light or radiation source within the handle 11 includes a lineally-mounted incandescent filament or ribbon 13 that is disposed within a parabolic reflector 15 which is oriented to direct the radiant energy from the filament toward the cutting edge 17 and facets 16 at the lower portion 18 of the blade. The lineally-mounted filament 13 assures adequate distribution of the radiant energy therefrom substantially over the length of the cutting edge 17 of blade 9. The electrical power to heat the filament 13 is applied thereto by A.C. or D.C. source 20 via conductors 21 and 22. A photodetector 30 is coupled to the internal structure of the blade 9 and is electrically coupled to the power source 20 through a conventional servo-regulator means 31 in a manner which controls the average power applied to the filament 13 in response to the level of radiant flux detected by photodetector 30.

Referring now to FIG. 2, there is shown a cross section of the apparatus of FIG. 1 including the filament 13 and the reflector 15 that directs radiant flux 5 substantially toward the facets 16 and cutting edge 17 of the blade 9. The filament 13, parabolic reflector 15 and radiation-transmitting window 14 may be formed into a chamber which is evacuated or filled with inert gas to minimize oxidation of the incandescent filament 13. The material of blade 9 should transmit and scatter well the radiant energy at the wavelengths of flux 5 from filament 13 but should absorb poorly or not at all at these wavelengths. A reflective optical coating 8 is disposed over the parabolic reflector and over the internal surfaces of the blade side walls 6 and 7 and the facets 16 of blade 9, but not over the window 14 through which the flux from the filament 13 is coupled to the blade 9. A layer 10 of radiation-absorbing, thermochromic material is disposed at the facets 16 of blade 9 adjacent the reflective coating 8 and acts as a collector of the radiant flux 5 from filament 13. The radiant flux 5 collected in layer 10 is converted to heat which is conducted to the cutting edge 17.

Thermochromic materials which have absorption coefficients that vary as a function of temperature may be used as the radiation-absorbing material of layer 10. Materials which exhibit thermochromic properties in selected temperature ranges include indium antimonide, gallium antimonide, and other semiconductors, zinc oxide, some lead salts, and other inorganic and organic materials.

Only a portion of the radiation which illuminates the absorbing material of layer 10 is absorbed. The remaining non-absorbed portion of the radiation is transmitted through the layer 10 and is internally reflected by the reflective coating 8 back through the layer 10 (where further absorption occurs) and re-emerges in the relatively transparent region 9 of the blade which is remote from the cutting edge where it follows a multi-reflective distribution path. As the temperature of the absorbing material 10 and hence of the cutting edge 17 increases, absorption by the material of layer 10 decreases and the average radiant flux in the transparent region 9 of the blade increases. Conversely, as the heated regions of the cutting edge 17 cool upon contact with tissue being cut, radiation absorption by the material of layer 10 increases and the average radiant flux in the transparent region 9 of the blade decreases. The radiant energy detector 30 may be coupled to the interior of the blade for monitoring the average radiant flux within the blade to increase or decrease the power supplied by the source 20 to the radiation source 13 as required.

Absorption by layer 10 of the wavelengths of radiant energy produced by filament 13 thus experiences increments for temperature decrements within the operating range of the cutting edge, which is within 300° C. to 1000° C. It is this radiation absorption property of the material of layer 10 that provides the self-regulating means by which local regions of the cutting edge 17 that cool upon contact with tissue being cut are radiantly heated by increased absorption of radiation. Other local regions of the cutting edge not cooled upon contact with tissue being cut do not exhibit increased absorption and therefore do not substantially change in their conversion of radiant energy to heat. Thus, as the temperature varies in various regions of facets 16 and the layer 10 disposed thereon, the radiation absorption of these regions vary inversely to assure radiation absorption of the cooled regions sufficient to maintain the operating temperature thereof within the desired operating range.

As the layer 10 and cutting edge 17 heat up prior to cutting, the layer 10 becomes less absorptive and higher levels of radiant flux 5 are reflected from layer 10 or are transmitted through layer 10 to be internally reflected by the reflecting surface 8. This increases the light flux within the relatively transparent material such as glass or quartz, or the like, of blade 9. Radiation scattering centers such as rutile fibers, quartz particles, or the like, may be dispersed through the region 9 of the blade. The increased light flux in region 9 is detected by detector 30 which is coupled through a conventional servo-regulator 31 to the power source 20 to decrease the power supplied to filament 13. The temperature of layer 10 and cutting edge 17 and facets 16 is thus stabilized within a preselected operating range. Conversely, as portions of the cutting edge 17 and facets 16 are cooled upon contact with tissue being cut, the material of layer 10 in the locally-cooled regions increases the absorption of radiant flux and decreases the level of flux in the portion of blade 9 sensed by detector 30, and this acts through servo-regulator 31 to increase the power supplied by power source 20 to the filament 13. Where it is desirable to maintain a relatively uniform wavelength spectrum of radiant energy over the dynamic range of power dissipation of the cutting instrument, the amount of surface area of the filament 13 heated to a specified temperature may be varied, as by retracting into the handle, or rotating within an aperture to vary the amount of radiant flux, rather than varying the temperature of the filament operating with a fixed, exposed area.

Alternatively, a relatively fixed spectrum can be accomplished by utilizing a filter between window 14 and the blade. Such a filter may also be used to narrow the bandwidth of the radiant energy, and thereby simplify the selection of absorbing materials used in layer 10 or, the filament 13 may be replaced by the ionized gas column of a gas discharge tube which emits radiant energy within one or a few characteristically narrow spectral lines, and which thus also simplifies the selection of absorbing materials used in layer 10.

Referring now to FIGS. 3 and 4, there are shown side and end views, respectively, of an alternative embodiment of the present invention in which the radiant source is disposed remotely from the cutting instrument. Light pipe elements such as fiber optic filaments 33 are aligned in a linear array to irradiate the absorbing layer 10. A photodetector 30 may be disposed within the handle 11 to detect the level of radiant flux and to produce a control signal on line 35 in response thereto for controlling the power output from the remote source 37, such as a laser. Alternatively, selected fibers in the array 33 can be used to sample radiant flux at locations along the length of the blade and illuminate a remote photodetector, thereby to produce the requisite power-controlling signal. Also, other optical means such as reflective mirrors and lenses may be used instead of the optical fibers to couple the radiant energy from the remote source into the absorbing layer 10.

FIG. 5 illustrates still another embodiment of the present invention in which the material of the absorbing layers 10a, 10b, 10c, etc. exhibits relatively constant absorption characteristic for converting radiant energy into heat for heating cutting edge 17 and also serves as an infrared radiation source whose radiation is a measure of its temperature. The illuminating 41a, 43a, etc. and detecting 41b, 43b, etc. fibers going to and coming from short segments of absorbing layer 10a, 10b, 10c, etc. can be gathered into two separate bundles for each segment. By utilizing a separate radiant source 47, 49, 51, etc. to illuminate the radiation absorbing material of each segment 10a, 10b, 10c, etc. and a separate detector for each source associated with each return fiber 41a, 41b, 41c, etc., the temperature of each segment can be independently monitored and the power output of the corresponding radiant source can be independently regulated so that the temperature of each segment along the cutting edge 17 can be maintained within a suitably constant temperature range, independent of the other segments along the cutting edge. Utilizing this principle, a rapidly-responding radiant source and detector may be time-shared among several segments along the length of the cutting edge 17. Further, a plurality of individual filaments of the type previously described with reference to FIGS. 1 and 2 may be lineally positioned along the length of the cutting edge 17 in order to independently elevate and regulate the temperature of a corresponding segment, independently of the temperature of an adjacent segment.

We claim:

1. A blade comprising:
   cutting means including a cutting edge, said cutting means being substantially transparent to radiant energy applied through said cutting means to said cutting edge;
   a radiant energy obsorbtive means disposed in the region of said cutting edge;
   and means for altering the radiant energy applied through said cutting means for maintaining the cutting means temperature within a selected operating range.

2. A blade as in claim 1 comprising:
   source means of radiant energy disposed to irradiate the radiant-energy absorptive means.

3. A hemostatic cutting device as in claim 2 wherein said source means of radiant energy includes an incandescent filament substantially linearly mounted along a portion of the length of the blade means.

4. A hemostatic cutting device as in claim 2 comprising a reflector means coupling radiant energy from the source means toward the radiant-energy absorptive means disposed in the region of said cutting edge.

5. A blade as in claim 2 wherein said source means includes a gas-discharge source.

6. A blade as in claim 5 wherein said gas-discharge source includes a laser.

7. A blade as in claim 2 comprising:
   photoresponsive means disposed to produce a control signal in response to the level of radiant energy within the blade; and
   means coupled to said photoresponsive means and to said source means of radiant energy for altering the level of radiant energy produced thereby.

8. A blade as in claim 1 comprising radiant-energy scattering means disposed within the blade for dispersing therewith radiant energy.

9. A hemostatic cutting device as in claim 1 wherein said radiant-energy absorptive means exhibits increased absorption in response to a decrease in temperature over a portion of the temperature range between approximately 300° C. and 1000° C.

10. A hemostatic cutting blade as in claim 1 comprising radiant-energy reflective means disposed on surfaces of the blade to contain radiant energy therein.

11. A hemostatic cutting blade as in claim 1 wherein the radiant-energy absorptive means exhibits increased reflectance for increased temperature over a portion of the temperature range between approximately 300° C. and 1000° C.

12. A hemostatic cutting instrument as in claim 1 wherein the radiant-energy absorptive means exhibits increased transmission of radiant energy for increased temperature over a portion of the temperature range between approximately 300° C. and 1000° C.

13. A hemostatic cutting blade instrument as in claim 1 comprising optical fibers for introducing radiant energy into said blade means.

14. A hemostatic cutting blade comprising:
   cutting means including a tissue cutting edge, said cutting means being substantially transparent to radiant energy applied through said blade means to said tissue cutting edge; and
   a radiant energy absorptive means which is characterized by an absorption which varies in response to temperature over a predetermined temperature range, said radiant energy absorptive means being disposed in the region of said cutting edge.

15. The hemostatic cutting blade claimed in claim 14 wherein said blade means is further defined as having radiant energy scattering means disposed therein.

16. The method of cutting using a substantially transparent blade means having a cutting edge operating at an elevated temperature, the method comprising:
   introducing radiant energy into the substantially transparent blade means; and absorbing radiant energy in the region of the cutting edge.

17. The method of cutting as in claim 16 including automatically absorbing increased amounts of radiant energy in regions of the cutting edge in response to a cooling of the edge in said regions.

18. The method of cutting using a blade means having a cutting edge operating at an elevated temperature the method comprising:
introducing radiant energy into a substantially transparent blade means; and
absorbing radiant energy in the region of the cutting edge.

19. The blade as in claim 1 where the temperature in the region of the cutting edge is elevated in response to radiant energy applied thereto.

* * * * *